(12) United States Patent
Sato et al.

(10) Patent No.: US 9,895,084 B2
(45) Date of Patent: Feb. 20, 2018

(54) BLOOD PRESSURE MEASUREMENT APPARATUS AND CONTROL METHOD FOR THE SAME

(71) Applicant: OMRON HEALTHCARE Co., Ltd., Kyoto (JP)

(72) Inventors: Hironori Sato, Kyoto (JP); Hiroyuki Kinoshita, Kyoto (JP); Toshihiko Ogura, Kyoto (JP)

(73) Assignee: OMRON HEALTHCARE Co., Ltd., Kyoto (JP)

( * ) Notice: Subject to any disclaimer, the term of this patent is extended or adjusted under 35 U.S.C. 154(b) by 273 days.

(21) Appl. No.: 14/656,379

(22) Filed: Mar. 12, 2015

(65) Prior Publication Data

US 2015/0182147 A1 Jul. 2, 2015

Related U.S. Application Data

(63) Continuation of application No. PCT/JP2013/070622, filed on Jul. 30, 2013.

(30) Foreign Application Priority Data

Sep. 25, 2012 (JP) ................................. 2012-211139

(51) Int. Cl.
*A61B 5/02* (2006.01)
*A61B 5/107* (2006.01)
(Continued)

(52) U.S. Cl.
CPC ........ *A61B 5/1075* (2013.01); *A61B 5/02108* (2013.01); *A61B 5/02225* (2013.01);
(Continued)

(58) Field of Classification Search
CPC .............. A61B 5/1075; A61B 5/02108; A61B 2560/0261; A61B 5/1071; A61B 5/6824;
(Continued)

(56) References Cited

U.S. PATENT DOCUMENTS

| 6,336,901 B1 * | 1/2002 | Itonaga .............. A61B 5/02141 600/499 |
| 2004/0024324 A1 * | 2/2004 | Bratteli .................. A61B 5/022 600/490 |

(Continued)

FOREIGN PATENT DOCUMENTS

| CN | 1400882 A | 3/2003 |
| JP | 2000-350706 A | 12/2000 |

(Continued)

OTHER PUBLICATIONS

International Search Report issued in corresponding International Application No. PCT/JP2013/070622 dated Aug. 27, 2013, and English translation thereof (4 pages).

(Continued)

*Primary Examiner* — Christian Jang
*Assistant Examiner* — Andrey Shostak
(74) *Attorney, Agent, or Firm* — Osha Liang LLP

(57) ABSTRACT

A CPU of a blood pressure measurement apparatus configured to be used while attached to a wrist of a measurement subject calculates an inclination angle formed by a forearm of the measurement subject with respect to a reference plane, and a rotation angle about an axis, where the forearm is used as the axis, of the blood pressure measurement device, based on information detected by an acceleration sensor, and uses the distance d between the radial artery and the ulnar artery that pass through the wrist, the inclination angle, and the rotation angle to determine the relative positional relationship between the radial artery and the ulnar artery. In accordance with the relative positional relationship, the CPU guides the measurement orientation of the measurement subject.

7 Claims, 10 Drawing Sheets

(51) Int. Cl.
  *A61B 5/022* (2006.01)
  *A61B 5/00* (2006.01)
  *A61B 5/021* (2006.01)

(52) U.S. Cl.
  CPC .......... *A61B 5/1071* (2013.01); *A61B 5/1079* (2013.01); *A61B 5/681* (2013.01); *A61B 5/6824* (2013.01); *A61B 2560/0261* (2013.01)

(58) Field of Classification Search
  CPC .... A61B 5/1079; A61B 5/02225; A61B 5/681
  See application file for complete search history.

(56) References Cited

U.S. PATENT DOCUMENTS

| | | | | |
|---|---|---|---|---|
| 2004/0077958 | A1* | 4/2004 | Kato | A61B 5/021 600/490 |
| 2010/0049059 | A1* | 2/2010 | Ha | A61B 5/021 600/485 |
| 2010/0125212 | A1* | 5/2010 | Kim | A61B 5/022 600/485 |
| 2010/0305418 | A1* | 12/2010 | Deliwala | A61B 5/14551 600/324 |

FOREIGN PATENT DOCUMENTS

| | | |
|---|---|---|
| JP | 2001-178694 A | 7/2001 |
| JP | 2002-541894 A | 12/2002 |
| JP | 2003-102693 A | 4/2003 |
| JP | 2003-144397 A | 5/2003 |
| JP | 2010-051364 A | 3/2010 |
| JP | 2011-224144 A | 11/2011 |
| WO | 02/39893 A1 | 5/2002 |

OTHER PUBLICATIONS

Office Action in counterpart Chinese Patent Application No. 201380046036.7, dated Jan. 4, 2016 (10 pages).

* cited by examiner ial artery or the ulnar artery differs from the height of the heart, the blood pressure value determined using the composite wave will include an error.

In Patent Documents 1 to 4, no consideration is given to the heights of the radial artery and the ulnar artery.

BLOOD PRESSURE MEASUREMENT APPARATUS AND CONTROL METHOD FOR THE SAME

TECHNICAL FIELD

The present invention relates to a wrist-type blood pressure measurement apparatus configured to be used while attached to a wrist, and a control method for the same.

BACKGROUND ART

With a wrist-type blood pressure measurement apparatus, in order to correctly measure the blood pressure, measurement needs to be started when the height of the wrist to which the cuff is attached and the height of the heart are approximately the same. For this reason, various methods for matching the height of the wrist and the height of the heart have been proposed in the past (e.g., see Patent Documents 1 to 4).

Patent Document 1 discloses a blood pressure measurement apparatus according to which, on the premise of a usage mode in which a measurement subject performs attachment of a blood pressure meter to his or her wrist while his or her forearm is on a table and thereafter raises the height of the wrist by lifting the forearm from the elbow, the distance between the wrist and the heart of the measurement subject is measured by a sensor, and the height of the wrist is determined based on the distance.

Patent Document 2 discloses a blood pressure measurement device that uses the forearm roll angle and pitch angle to determine the height of the measurement site.

Patent Document 3 discloses a blood pressure measurement device that, by starting blood pressure measurement while the measurement site is in contact with the chest, allows blood pressure measurement in a state in which the heights of the measurement site and the heart match.

Patent Document 4 discloses a blood pressure measurement apparatus that determines the suitability of the blood pressure measurement based on the orientation of a user detected by a biaxial acceleration sensor and performs notification of the determination result.

CITATION LIST

Patent Literature

Patent Document 1: JP 2001-178694A
Patent Document 2: WO 2002/39893A
Patent Document 3: JP 2010-51364A
Patent Document 4: JP 2003-102693A

SUMMARY OF INVENTION

Two arteries pass through the wrist, namely the ulnar artery, which is located along the ulna on the pinky finger side, and the radial artery, which is located along the radius on the thumb side. For this reason, if the pressurizing pressure of a cuff is transferred evenly without loss to the ulnar artery and the radial artery, a blood pressure value measured using an oscillometric method is determined using a wave obtained by compositing the pulse wave generated in the radial artery and the pulse wave generated in the ulnar artery.

As long as the respective heights of the radial artery and the ulnar artery are the same as the height of the heart, the blood pressure value determined using the composite wave will be an accurate value. However, if the height of the radial artery or the ulnar artery differs from the height of the heart, the blood pressure value determined using the composite wave will include an error.

In Patent Documents 1 to 4, no consideration is given to the heights of the radial artery and the ulnar artery.

Therefore one or more embodiments of the claimed invention provides a wrist-type blood pressure measurement apparatus and a control method for the same, according to which the blood pressure measurement accuracy can be raised.

The blood pressure measurement apparatus according to one or more embodiments of the claimed invention is a blood pressure measurement apparatus configured to be used while attached to a wrist of a measurement subject, including: an inclination angle measurement unit configured to measure an inclination angle, which is an angle formed by the forearm of the measurement subject with respect to a reference plane; a rotation angle measurement unit configured to measure a rotation angle about an axis, using a forearm as the axis, of the blood pressure measurement apparatus; a distance information acquisition unit configured to acquire distance information regarding the distance between the ulnar artery and the radial artery that pass through the wrist; a determination unit configured to determine a relative positional relationship between the radial artery and the ulnar artery using the inclination angle, the rotation angle, and the distance information; and a control unit configured to perform control according to the relative positional relationship.

The control method for the blood pressure measurement apparatus according to one or more embodiments of the claimed invention is a control method for a blood pressure measurement apparatus configured to be used while attached to a wrist of a measurement subject, the method including: an inclination angle measurement step of measuring an inclination angle, which is an angle formed by a forearm of the measurement subject with respect to a reference plane; a rotation angle measurement step of measuring a rotation angle about an axis, using the forearm as the axis, of the blood pressure measurement apparatus; a distance information acquisition step of acquiring distance information regarding the distance between the radial artery and the ulnar artery, which pass through the wrist; a determination step of determining a relative positional relationship between the radial artery and the ulnar artery using the inclination angle, the rotation angle, and the distance information; and a control step of performing control according to the relative positional relationship.

Advantageous Effects of Invention

According to one or more embodiments of the claimed invention, it is possible to provide a wrist-type blood pressure measurement apparatus and a control method for the same, according to which the blood pressure measurement accuracy can be raised.

DESCRIPTION OF EMBODIMENTS

Hereinafter, an embodiment of the claimed invention will be described with reference to the drawings.

Figure 1:
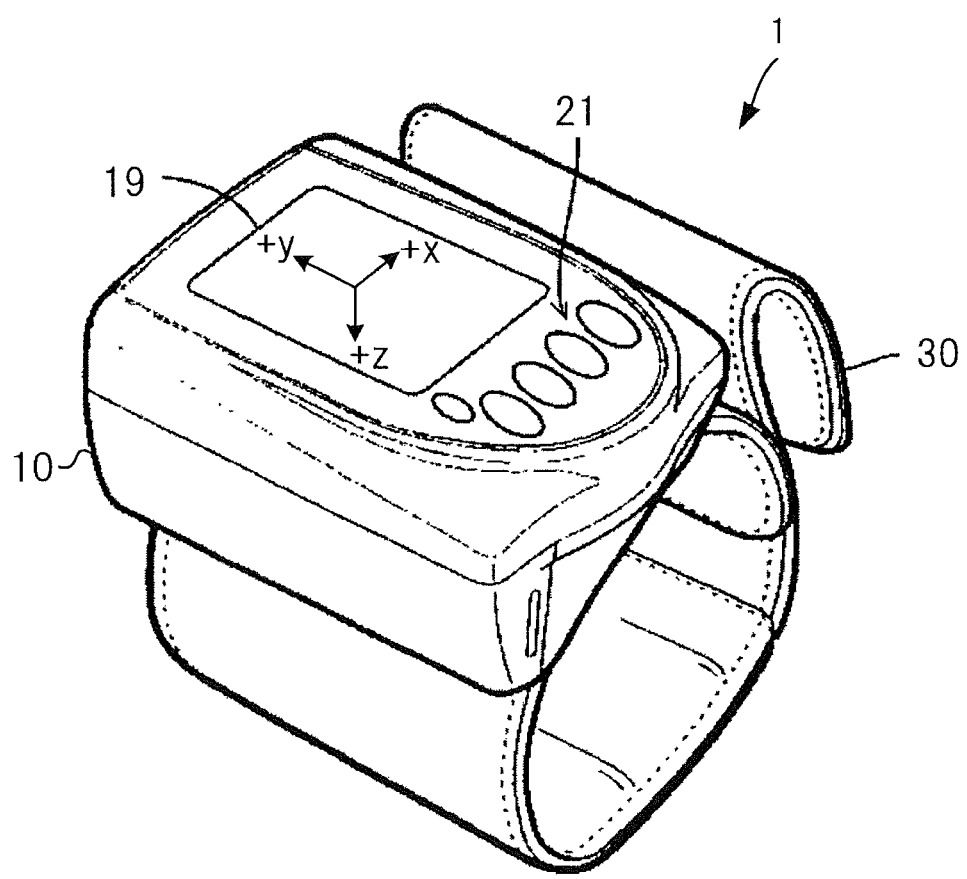
FIG. 1 is an external appearance diagram showing an overall configuration of a wrist-type blood pressure measurement apparatus 1 for describing an embodiment of the claimed invention.

FIG. 1 is an external appearance diagram showing an overall configuration of a wrist-type blood pressure measurement apparatus 1 for describing an embodiment of the claimed invention.

The blood pressure measurement apparatus 1 includes a main body portion 10 and a cuff 30 that can be wrapped around a wrist of a measurement subject. The main body portion 10 is attached to the cuff 30. The cuff 30 includes an air bladder 31 (see FIG. 2), and an air tube 40 is connected to the air bladder 31.

A display unit 19 constituted by liquid crystal and the like for example, and an operation unit 21 for receiving an instruction from a user (measurement subject) are arranged on the surface of the main body portion 10. The operation unit 21 includes multiple switches.

In the present specification, "cuff" refers to a belt-shaped or tube-shaped structure that has an inner cavity and can be wrapped around a measurement site of a body (wrist), and it indicates an object that is used to measure blood pressure by pressurizing an artery of a measurement subject with insertion of a fluid such as air or a liquid into the inner cavity.

A later-described acceleration sensor 17 is built into the main body portion 10. The acceleration sensor 17 is a triaxial gravitational acceleration sensor that detects weight acceleration in three directions, namely an x axis direction, a y axis direction, and a z axis direction, shown in FIG. 1. Note that the display surface of the display unit 19 is parallel with the xy plane.

Figure 2:
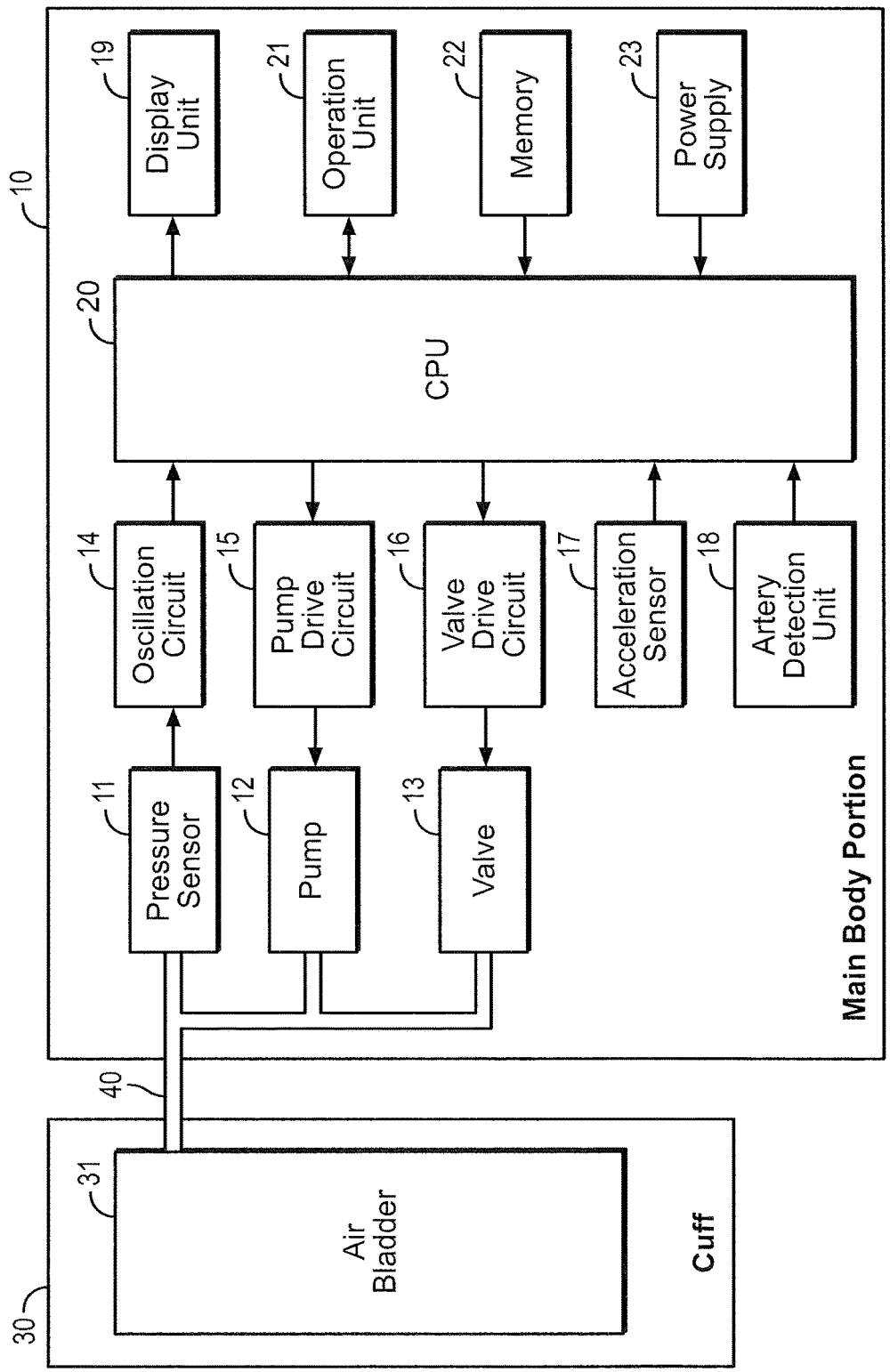
FIG. 2 is a diagram showing an internal configuration of the blood pressure measurement apparatus 1 shown in FIG. 1.

FIG. 2 is a diagram showing an internal configuration of the blood pressure measurement apparatus 1 shown in FIG. 1.

The main body portion 10 includes a pressure sensor 11, a pump 12, and an exhaust valve (called simply a "valve" hereinafter) 13 that are connected to the air tube 40, an oscillation circuit 14, a pump drive circuit 15, a valve drive circuit 16, an acceleration sensor 17, an artery detection unit 18, the display unit 19, a control unit (CPU) 20 that performs overall control of the main body portion 10 and carries out various types of computational processes, the operation unit 21, a memory 22, and a power supply 23 that supplies power to the units of the main body portion 10.

The pump 12 supplies air to the air bladder 31 in order to increase the pressure with which the cuff 30 pressurizes the measurement site (referred to below as "cuff pressure" as well).

The valve 13 is opened and closed in order to discharge air from or seal air in the air bladder 31.

The pump drive circuit 15 controls the driving of the pump 12 based on a control signal obtained from the CPU 20.

The valve drive circuit 16 controls the opening and closing of the valve 13 based on a control signal obtained from the CPU 20.

The pressure sensor 11 is a sensor that converts the air pressure in the air bladder 31 of the cuff 30 into an electrical signal (cuff pressure signal). An electrostatic capacitance pressure sensor, for example, is used for the pressure sensor 11. With an electrostatic capacitance pressure sensor, a capacitance value changes in accordance with a detected electrical signal.

The oscillation circuit 14 oscillates based on the capacitance value of the pressure sensor 11 and outputs a signal in accordance with that capacitance value to the CPU 20. The CPU 20 detects the pressure in the cuff 30 by acquiring the cuff pressure signal output from the oscillation circuit 14.

The memory 22 includes a read-only memory (ROM) that stores programs, data, and so on for causing the CPU 20 to perform predetermined operations, a random access memory (RAM) used as a working area, and a flash memory that holds measured blood pressure data and the like.

When the blood pressure measurement apparatus 1 is attached to a wrist of the measurement subject, the artery detection unit 18 detects the positions of the radial artery and the ulnar artery located in the wrist.

The artery detection unit 18 is constituted by a light emitting element (e.g., an LED) that emits light (e.g., infrared) and a photoelectric conversion element that receives light emitted from the light emitting element and reflected from the wrist and converts it into an electrical signal. It is sufficient that the light emitted from the light emitting element has a wavelength that can reach the interior of the body.

By lining up pairs that each consist of a light emitting element and a photoelectric conversion element in a one-dimensional shape or a two-dimensional shape, it is possible to perform imaging of the radial artery and the ulnar artery located in the wrist, and the positions of the radial artery and the ulnar artery can be detected.

With the blood pressure measurement apparatus 1, an inclination angle θ1, which is an angle formed by the forearm of the measurement subject with respect to a reference plane, and a rotation angle θ2 of the blood pressure measurement apparatus 1 about an axis using the forearm of the measurement subject as the axis can be measured according to the information detected by the acceleration sensor 17. Hereinafter, the inclination angle θ1 and the rotation angle θ2 will be described in detail.

Figure 3:
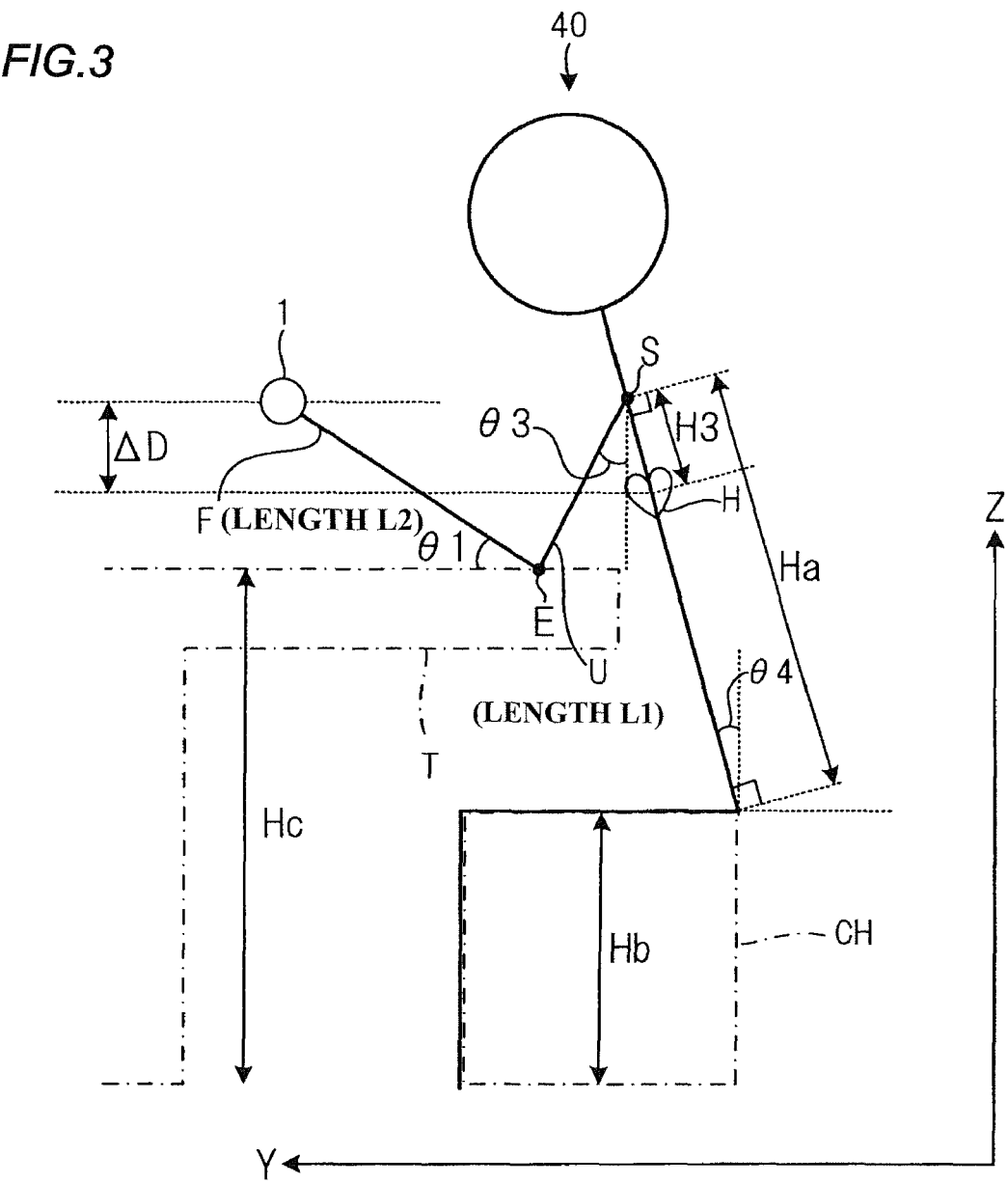
FIG. 3 is a diagram showing an exemplary usage mode of the blood pressure measurement apparatus 1 shown in FIG. 1.
Figure 4:
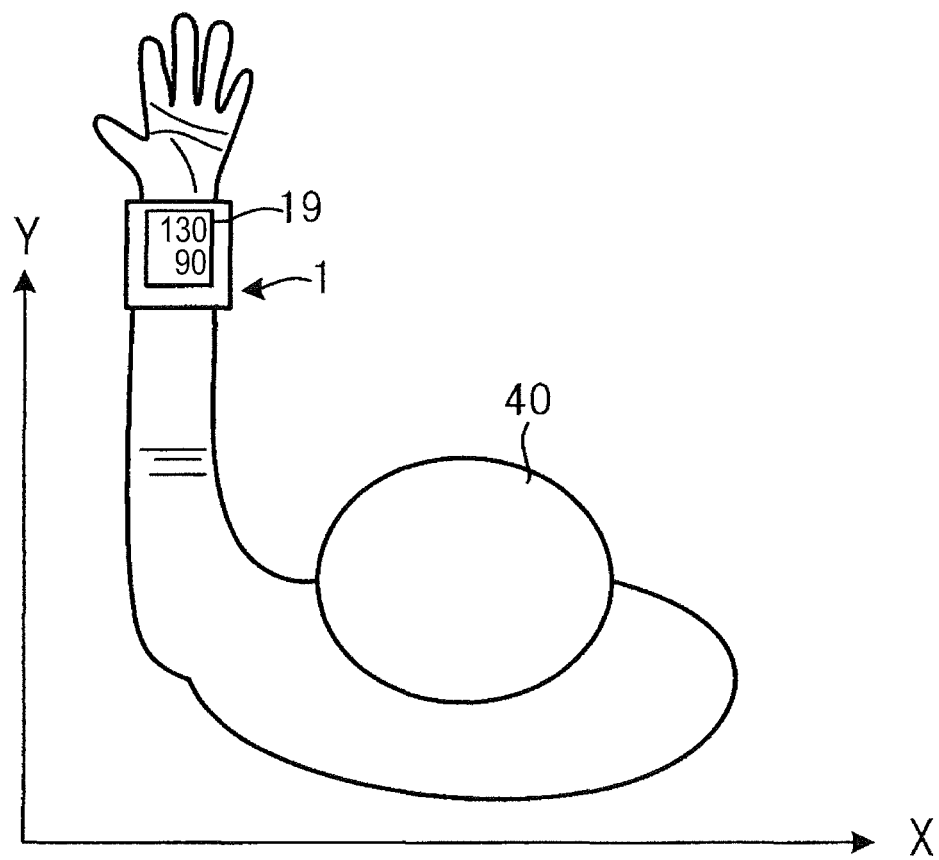
FIG. 4 is a view of FIG. 3 from the head portion of a measurement subject 40.

FIG. 3 is a diagram showing an example of a usage state of the blood pressure measurement apparatus 1. FIG. 4 is a diagram showing a case where the usage state shown in FIG. 3 is viewed from above the head of a measurement subject 40. In FIGS. 3 and 4, the xy plane is a plane parallel to the ground, and the z axis direction is the gravity direction.

As shown in FIG. 3, the blood pressure measurement apparatus 1 is used in a state in which the measurement subject 40 sits in a chair CH and places his or her elbow E on a table T.

In FIG. 3, reference letter S indicates the shoulder of the measurement subject 40, reference letter U indicates the upper arm of the measurement subject 40, and reference letter F indicates the forearm of the measurement subject 40.

As shown in FIG. 4, the blood pressure measurement apparatus 1 is used while attached to the wrist of the measurement subject such that the display surface of the display unit 19 provided on the main body portion 10 is parallel with the palm of the measurement subject 40.

Also, upon the measurement subject 40 attaching the blood pressure measurement apparatus 1 to his or her wrist, use of the blood pressure measurement apparatus 1 is started in an orientation in which the elbow and wrist are on the table T (hereinafter referred to as "assumed orientation").

As shown in FIG. 3, the angle formed by the forearm F with respect to the upper surface of the table T, which is the reference plane, is the inclination angle θ1. It is sufficient that the reference plane is a plane that is parallel to the xy plane and is below the elbow E, and for example, it may be the ground.

Figure 5:
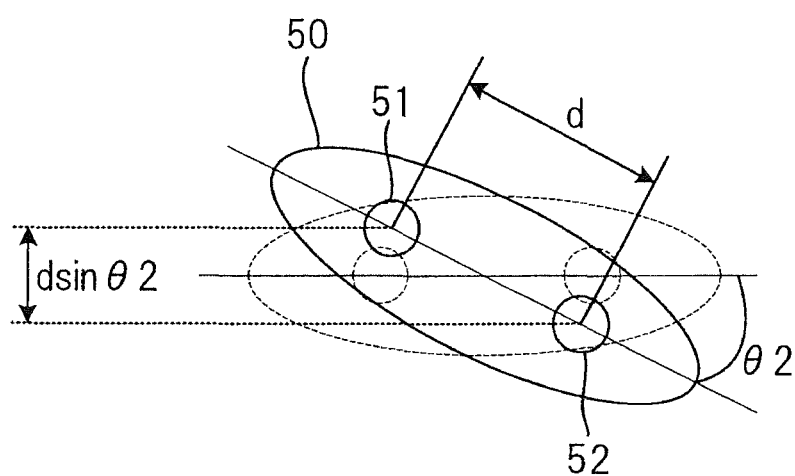
FIG. 5 is a diagram showing a cross-section of a wrist of a measurement subject.

FIG. 5 is a diagram showing a cross-section in a direction orthogonal to the direction in which the forearm of the wrist 50 to which the blood pressure measurement apparatus 1 is attached extends. Reference numeral 51 indicates the radial artery and reference numeral 52 indicates the ulnar artery.

In FIG. 5, the portion indicated by the broken line indicates the position of the wrist 50 in the assumed orientation. A state in which the wrist 50 has been rotated about an axis, using the forearm as the axis, from the assumed orientation is indicated by the solid line, and the rotation angle θ2 at that time can be measured based on the gravitational acceleration in the x axis direction of the acceleration sensor 17.

Also, in FIG. 5, a distance d between the radial artery and the ulnar artery can be obtained based on the image formed by the artery detection unit 18.

The difference in the heights from the reference plane of the radial artery and the ulnar artery in FIG. 5 is d sin θ2. Also, since the difference in the heights changes also due to the inclination angle θ1, the difference in the heights from the reference plane of the radial artery and the ulnar artery is obtained by calculation of d sin θ2×cos θ1.

Figure 6:
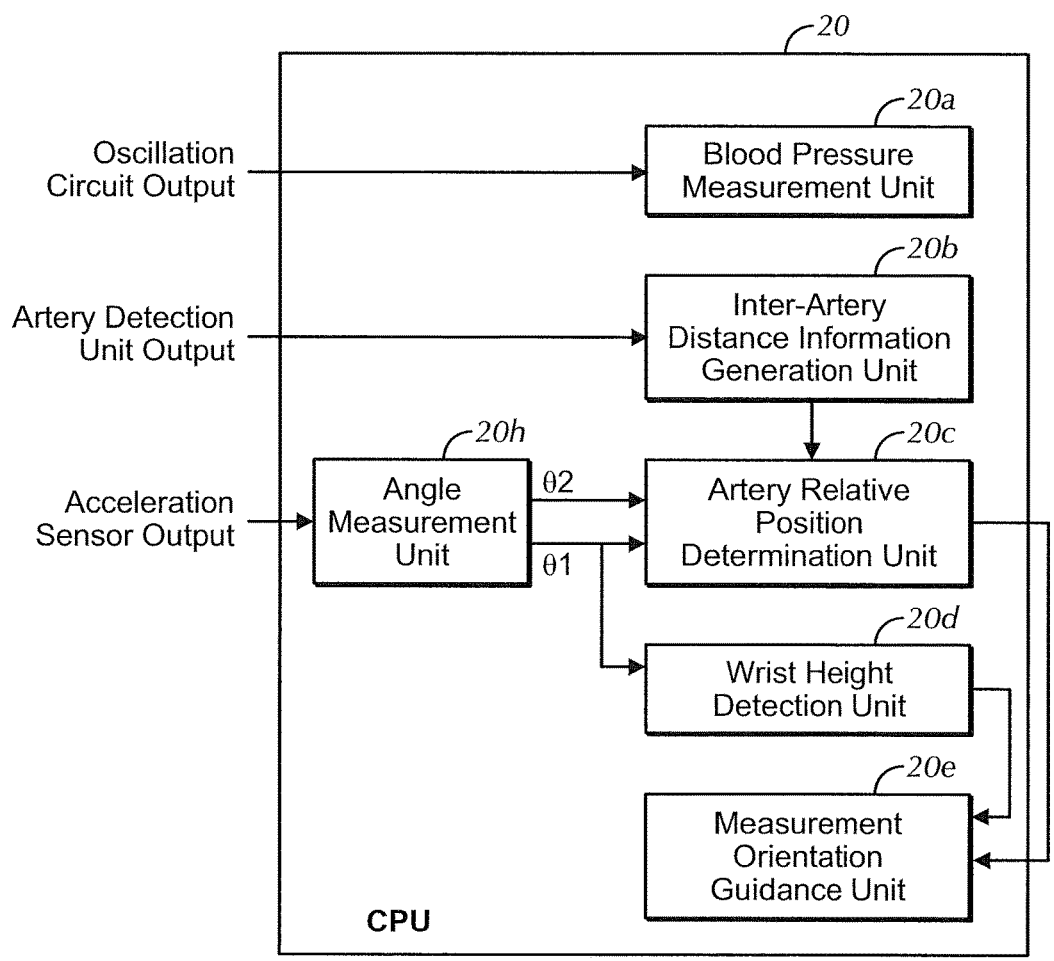
FIG. 6 is a functional block diagram of a CPU 20 shown in FIG. 2.

FIG. 6 is a diagram showing functional blocks realized by the CPU 20 shown in FIG. 2 reading out a program stored in the ROM and executing it.

The CPU 20 includes a blood pressure measurement unit 20a, an inter-artery distance information generation unit 20b, an artery relative position determination unit 20c, a wrist height detection unit 20d, a measurement orientation guidance unit 20e, and an angle measurement unit 20h.

These are functions realized in the CPU 20 mainly by the CPU 20 reading out programs stored in the memory 22 and executing them, but a portion or all of these functions may be realized using a hardware configuration.

The blood pressure measurement unit 20a extracts the pulse wave and the cuff pressure from the cuff pressure signal input from the oscillation circuit 14. The blood pressure measurement unit 20a calculates the amplitude value of the extracted pulse wave and creates pulse wave amplitude envelope data that corresponds to the amplitude value of the pulse wave and the cuff pressure at the time of pulse wave generation. The blood pressure measurement unit 20a uses the pulse wave amplitude envelope data to determine measured blood pressure values, namely the systolic blood pressure and diastolic blood pressure.

The inter-artery distance information generation unit 20b uses the imaging signal output from the artery detection unit 18 to generate distance information regarding the distance (d in FIG. 5) between the radial artery and the ulnar artery located in the wrist of the measurement subject.

The angle measurement unit 20h calculates the inclination angle θ1 and the rotation angle θ2 based on the output of the acceleration sensor 17.

The artery relative position determination unit 20c uses the inclination angle θ1 and the rotation angle θ2 generated by the angle measurement unit 20h, and the distance information d generated by the inter-artery distance information generation unit 20b to determine the relative positional relationship between the radial artery and the ulnar artery located in the wrist of the measurement subject.

As the relative positional relationship, the artery relative position determination unit 20c determines which of the radial artery and the ulnar artery is located at a higher position with respect to the reference plane (magnitude relationship between the heights of the radial artery and the ulnar artery), and determines how different the heights are in the case where either one is higher than the other.

The artery relative position determination unit 20c calculates the difference between the heights from the reference plane of the radial artery and the ulnar artery, that is ΔH, using equation (1) below, and determines the relative positional relationship based on ΔH.

Note that in FIG. 5, the rotation angle θ2 has a negative sign if the wrist rotates from the assumed orientation to the left, and has a positive sign if the wrist rotates from the assumed orientation to the right. For this reason, according to the sign of ΔH, it is possible to determine which of the radial artery and the ulnar artery is at a higher position.

$$\Delta H = d \times \sin \theta 2 \times \cos \theta 1 \qquad (1)$$

The wrist height detection unit 20d uses the inclination angle θ1 calculated by the angle measurement unit 20h and various types of information relating to the measurement subject that are stored in advance in the memory 22 to calculate the height, with respect to the heart, of the wrist of the measurement subject (height difference ΔD between the blood pressure measurement apparatus 1 and the heart of the measurement subject 40, shown in FIG. 3).

Note that the wrist height detection unit 20d calculates ΔD on the premise that the height from the reference plane of the blood pressure measurement apparatus 1 is the same as the height from the reference plane of the radial artery in the wrist to which the blood pressure measurement apparatus 1 is attached, or is the same as the height from the reference plane of the ulnar artery in the wrist to which the blood pressure measurement 1 is attached.

The information stored in advance in the memory 22 is upper arm length L1, forearm length L2, distance Ha from a shoulder S of the measurement subject 40 to the seat face of a chair CH, seat face height Hb of the chair CH, and height He of the table T. L1, L2, and Ha may be values that are automatically determined based on the height of the measurement subject 40. It is sufficient to use a configuration in which Hb and He can be input manually by the measurement subject.

In FIG. 3, letting the angle formed by the upper arm U of the measurement subject 40 and the gravity direction be θ3, and the distance from the shoulder S to the heart H be H3, ΔD is obtained using equation (2) below.

$$\Delta D = L2 \sin \theta 1 - \{L1 \cos \theta 3 - (H3 \cos \theta 4)\} \qquad (2)$$

Here, the distance H3 can be substituted by a value that is approximately half of the length L1 of the upper arm U.

Also, based on the equation L1 cos θ3=Ha cos θ4−(Hc−Hb), cos θ4 is obtained using equation (3) below.

$$\cos θ4 = \{L1 \cos θ3 + (Hc-Hb)\}/Ha \quad (3)$$

Here, since the angle θ3 is a value that is already known through experimentation, the angle θ3 is also stored in advance in the memory 22. Accordingly, the wrist height detection unit 20d can calculate the height, with respect to the heart, of the wrist of the measurement subject using an equation obtained by substitution of equation (3) into equation (2), the inclination angle θ1, and the information stored in the memory 22.

Note that the method for calculating the height of the wrist is not limited to the above description, and a well-known method such as that disclosed in Patent Document 1, 2, or the like can be used.

The measurement orientation guidance unit 20e outputs information for guiding the inclination angle θ1 so that ΔD, which was calculated by the wrist height detection unit 20d, becomes less than or equal to an allowable value. The allowable value is a value according to which the required blood pressure measurement accuracy is obtained.

For example, by displaying a message such as "Please tilt forearm forward slightly", or "Please tilt forearm back slightly" on the display unit 19, the measurement orientation guidance unit 20e guides the measurement subject so that ΔD becomes less than or equal to the allowable value.

Also, the measurement orientation guidance unit 20e outputs information for guiding the rotation angle θ2 so that ΔH (absolute value without a sign), which was calculated by the artery relative position determination unit 20c, becomes less than or equal to an allowable value. This allowable value is also a value according to which the required blood pressure measurement accuracy is obtained.

For example, by displaying messages such as "Please rotate wrist slightly to the right" and "Please rotate wrist slightly to the left" on the display unit 19, the measurement orientation guidance unit 20e guides the measurement subject so that ΔH (absolute value without a sign) becomes less than or equal to the allowable value.

Next, operations of the blood pressure measurement apparatus 1 with the above-described configuration will be described.

Figure 7:
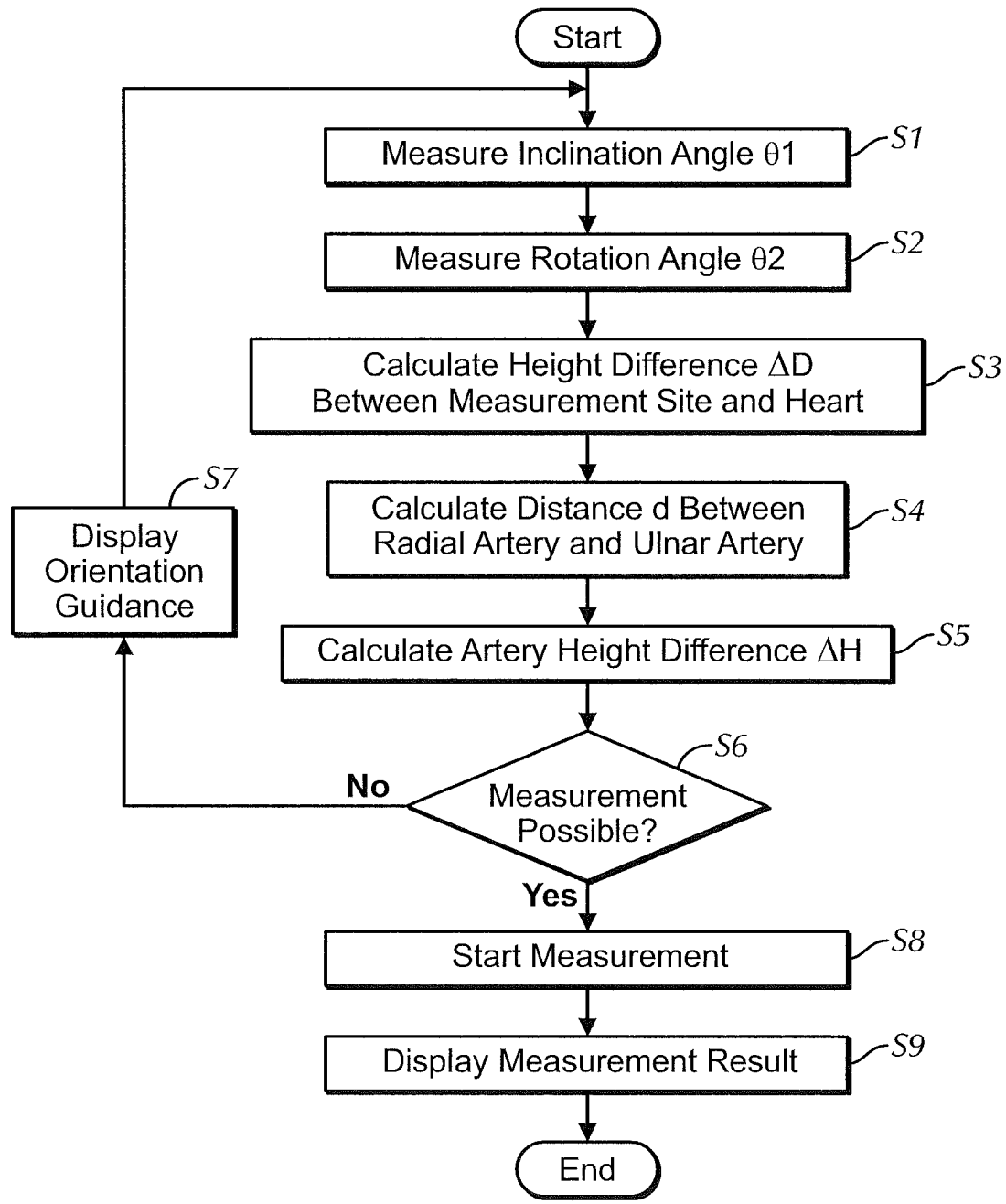
FIG. 7 is a flowchart for describing an operation of the blood pressure measurement apparatus 1 shown in FIG. 1.

FIG. 7 is a flowchart for describing an operation of the blood pressure measurement apparatus 1.

When the start of blood pressure measurement is instructed by operation of the operation unit 21, the CPU 20 measures the inclination angle θ1 of the forearm based on the information detected by the acceleration sensor 17 (step S1), and measures the rotation angle θ2 based on the information detected by the acceleration sensor 17 (step S2).

Also, the CPU 20 uses the inclination angle θ1 measured in step S1, and information regarding the upper arm length L1, the forearm length L2, the angle θ3, the distance Ha from the shoulder S of the measurement subject 40 to the seat face of the chair CH, the seat face height Hb of the chair CH, and the height Hb of the table T to calculate ΔD according to equations (2) and (3) (step S3).

Next, the CPU 20 calculates the distance d between the radial artery and the ulnar artery, based on the image formed by the artery detection unit 18 (step S4).

Then, the CPU 20 uses the inclination angle θ1 measured in step S1, the rotation angle θ2 measured in step S2, and the distance d calculated in step S4 to calculate ΔH according to the calculation of equation (1) (step S5).

Based on ΔD calculated in step S3 and ΔH calculated in step S5, the CPU 20 determines whether or not the orientation of the measurement subject is an orientation at which blood pressure measurement is possible (step S6).

If ΔD is less than or equal to the allowable value and ΔH is less than or equal to the allowable value, the CPU 20 determines that it is an orientation at which blood pressure measurement is possible. If one of ΔD and ΔH exceeds the allowable value, the CPU 20 determines that it is an orientation at which blood pressure measurement is not possible.

If the result of the determination in step S6 is NO, the CPU 20 calculates the inclination angle θ1 and the rotation angle θ2 according to which ΔD and ΔH both become less than or equal to the allowable value, and causes the display unit 19 to display information for guiding the measurement subject so that the inclination angle θ1 and the rotation angle θ2 become the calculated angles (step S7). Then, the CPU 20 returns to the processing of step S1.

Note that in step S7, the guidance is not limited to being performed using message display, and it is possible to guide the orientation using audio.

When the result of the determination in step S6 is YES, the CPU 20 starts inflating the cuff 30 and starts blood pressure measurement by means of an oscillometric method (step S8).

Upon determining the measured blood pressure value based on the pulse wave amplitude envelope data, the CPU 20 causes the display unit 19 to display the determined blood pressure value (step S9) and ends the operation according to the blood pressure measurement instruction.

As described above, according to the blood pressure measurement apparatus 1, it is possible to start blood pressure measurement in a state in which the difference between the heights from the reference plane of the radial artery and the ulnar artery, that is ΔH, is less than or equal to the allowable value. For this reason, it is possible to obtain a measured blood pressure value with little error, and it is possible to increase the reliability of the measured blood pressure value.

Note that as long as it is assumed that measurement is performed in a state in which the height of the wrist and the height of the heart are the same, the processing of step S3 in FIG. 7 can be omitted.

In that case, in step S6 in FIG. 7, it is determined whether or not the height difference ΔH between the two arteries is less than or equal to the allowable value, and if ΔH exceeds the allowable value, in step S7, it is sufficient to perform orientation guidance so that ΔH becomes less than or equal to the allowable value.

Also, although the artery detection unit 18 is provided in the blood pressure measurement apparatus 1, it may be omitted.

If the artery detection unit 18 is omitted, it is sufficient that the distance information regarding the distance between the radial artery and the ulnar artery is stored in advance in the memory 22 and the CPU 20 acquires the distance information from the memory 22 instead of performing step S4 in FIG. 7.

The distance information regarding the distance between the radial artery and the ulnar artery may be stored in the memory 22 by manual input by the measurement subject, and the manufacturer of the blood pressure measurement apparatus 1 may store the average value of the distance between the radial artery and the ulnar artery in the memory 22.

Also, although a description was given in which the blood pressure measurement unit 20a measures the blood pressure using an oscillometric method, it may measure the blood pressure using another method, such as a method of measuring the blood pressure by detecting a Korotkoff sound.

An example was described above in which blood pressure measurement is performed after guiding the orientation of the measurement subject so that the height difference ΔD between the wrist and the heart and the height difference ΔH between the radial artery and the ulnar artery become less than or equal to the allowable value.

Hereinafter, an example will be described in which blood pressure measurement is possible also in a state in which ΔH exceeds the allowable value and the accuracy of blood pressure measurement is raised by correcting the blood pressure measurement result.

Figure 8:
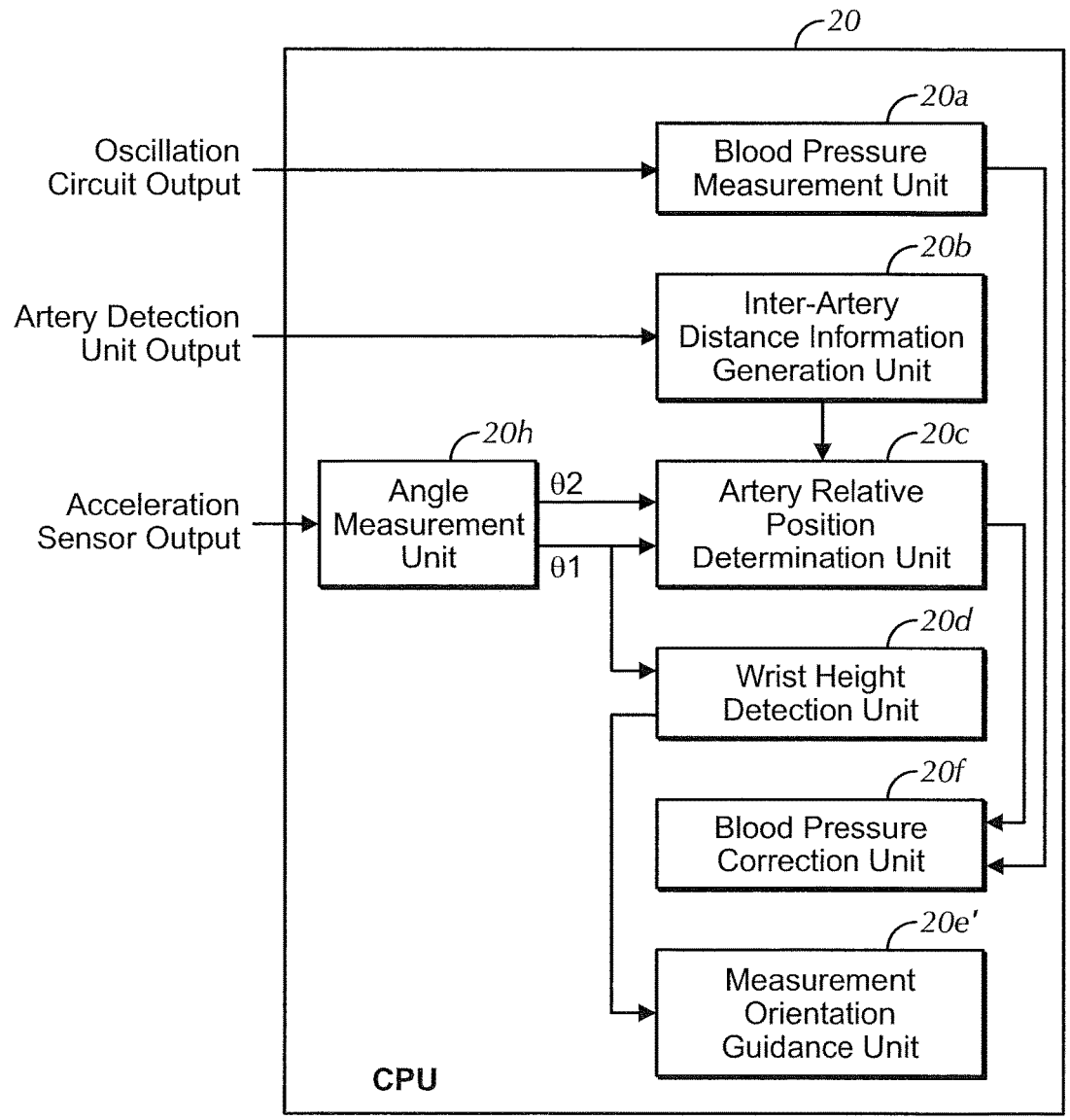
FIG. 8 is a diagram showing a modified example of functional blocks in the CPU 20 shown in FIG. 6.

FIG. 8 is a diagram showing a modified example of functional blocks in the CPU 20 shown in FIG. 6.

Aside from the fact that a measurement orientation guidance unit 20e' is provided instead of the measurement orientation guidance unit 20e and a blood pressure correction unit 20f has been added, the CPU 20 shown in FIG. 8 has the same configuration as in FIG. 6.

The measurement orientation guidance unit 20e' outputs information for guiding the orientation of the measurement subject so that the height difference ΔD between the wrist and the heart, which was calculated by the wrist height detection unit 20d, becomes less than or equal to the allowable value.

If ΔD, which was calculated by the wrist height detection unit 20d, is less than or equal to the allowable value, the blood pressure measurement unit 20a according to this modified example starts blood pressure measurement according to an oscillometric method and transmits the determined blood pressure value to the blood pressure correction unit 20f.

Based on the height difference ΔH between the radial artery and the ulnar artery, which was calculated by the artery relative position determination unit 20c, the blood pressure correction unit 20f corrects the measured blood pressure value determined by the blood pressure measurement unit 20a and causes the corrected blood pressure value to be displayed on the display unit 19.

Figure 9:
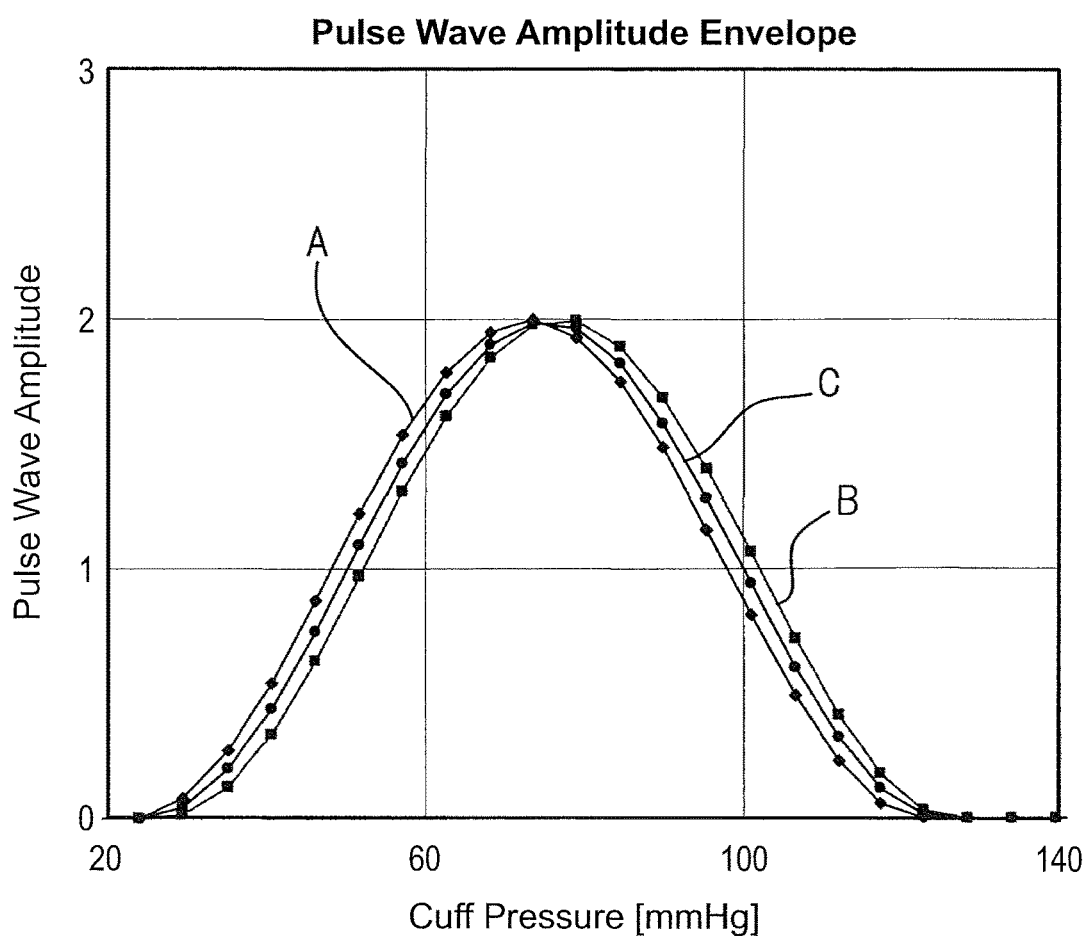
FIG. 9 is a diagram showing an example of a pulse wave amplitude envelope.
Figure 10:
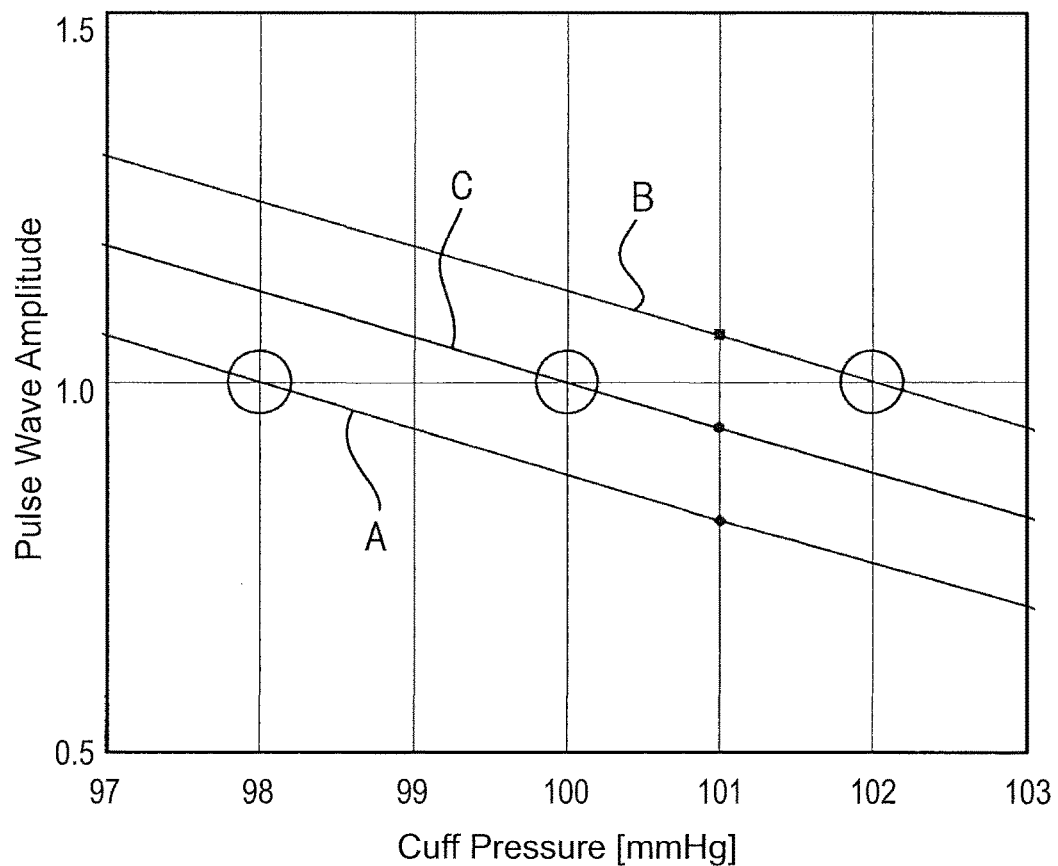
FIG. 10 is a partial enlarged view of FIG. 9.

FIG. 9 is a diagram showing an example of a pulse wave amplitude envelope. FIG. 10 is a partial enlarged view of FIG. 9. FIG. 9 shows an envelope A, an envelope B, and an envelope C.

The envelope A is a pulse wave amplitude envelope generated by the blood pressure measurement unit 20a in the case where all of the pressurizing pressure of the cuff 30 is transmitted to the radial artery without loss and the pressurization of the ulnar artery is insufficient.

The envelope B is a pulse wave amplitude envelope generated by the blood pressure measurement unit 20a in the case where all of the pressurizing pressure of the cuff 30 is transmitted to the ulnar artery without loss and the pressurization of the radial artery is insufficient.

The envelope C is a pulse wave amplitude envelope generated by the blood pressure measurement unit 20a in the case where all of the pressurizing pressure of the cuff 30 is transmitted to both the ulnar artery and the radial artery without loss.

Note that FIG. 9 shows data for when the height from the ground of the radial artery is 5 cm higher than the height from the ground of the ulnar artery (when ΔH=5 cm).

In the pulse wave amplitude envelope shown in FIG. 9, if the cuff pressure at which the pulse wave amplitude is 1 is determined as being the systolic blood pressure, the systolic blood pressure is 98 [mmHg] according to envelope A, the systolic blood pressure is 102 [mmHg] according to envelope B, and the systolic blood pressure is 100 [mmHg] according to envelope C.

In the present embodiment, it is assumed that the radial artery and the ulnar artery are pressurized uniformly by the cuff 30. In other words, the structure of the cuff 30 is designed such that the ratio of the transmission rate to the radial artery to the transmission rate to the ulnar artery of the pressurizing pressure of the cuff 30 is a:b=1:1.

Accordingly, if the heights of the radial artery and the ulnar artery do not match and one of the radial artery and the ulnar artery matches the height of the heart, an error caused by the height difference (above-described ΔH) occurs in the measured blood pressure value determined by the blood pressure measurement unit 20a.

If there is a height difference ΔH (cm) between the two arteries, a pressure difference obtained by multiplying ΔH by a hydraulic head pressure per unit length (=0.8 mmHg/cm) will appear in the two arteries.

For example, in the case where the radial artery is at a higher position than the ulnar artery, the pressure difference between the radial artery and the ulnar artery corresponds to the difference between the systolic blood pressure determined by the envelope A and the systolic blood pressure determined by the envelope B shown in FIG. 10.

Letting the ratio of the transmission rate to the radial artery to the transmission rate to the ulnar artery of the pressurizing pressure of the cuff 30 be a:b, the hydraulic head pressure be β, and the systolic blood pressure determined by the envelope C shown in FIG. 10 be P, the systolic blood pressure P' determined by the envelope A is determined using equation (4) below. Also, the systolic blood pressure P" determined by the envelope B is determined using equation (5) below.

$$P'=P-[\beta \times \Delta H \times \{a/(a+b)\}] \qquad (4)$$

$$P''=P+[\beta \times \Delta H \times \{b/(a+b)\}] \qquad (5)$$

In equations (4) and (5), the sign of ΔH is also considered.

In equations (4) and (5), P is a value determined by the blood pressure measurement unit 20a. Also, ΔH is a value calculated by the artery relative position determination unit 20c. Also, a and b are values determined by the structure of the cuff 30.

If the wrist height detection unit 20d calculates ΔD assuming that the height from the reference plane of the blood pressure measurement apparatus 1 is the same as the height from the reference plane of the radial artery in the wrist to which the blood pressure measurement apparatus 1 is attached, or in other words, if blood pressure measurement is started in a state in which the height of the heart and the height of the radial artery are almost the same, it is sufficient that the blood pressure correction unit 20f calculates P' above as the final blood pressure value.

On the other hand, if the wrist height detection unit 20d calculates ΔD assuming that the height from the reference plane of the blood pressure measurement apparatus 1 is the same as the height from the reference plane of the ulnar artery in the wrist to which the blood pressure measurement apparatus 1 is attached, or in other words, if blood pressure measurement is started in a state in which the height of the heart and the height of the ulnar artery are almost the same, it is sufficient that the blood pressure correction unit 20f calculates P" above as the final blood pressure value.

Hereinafter, an operation of the CPU 20 shown in FIG. 8 will be described.

Figure 11:
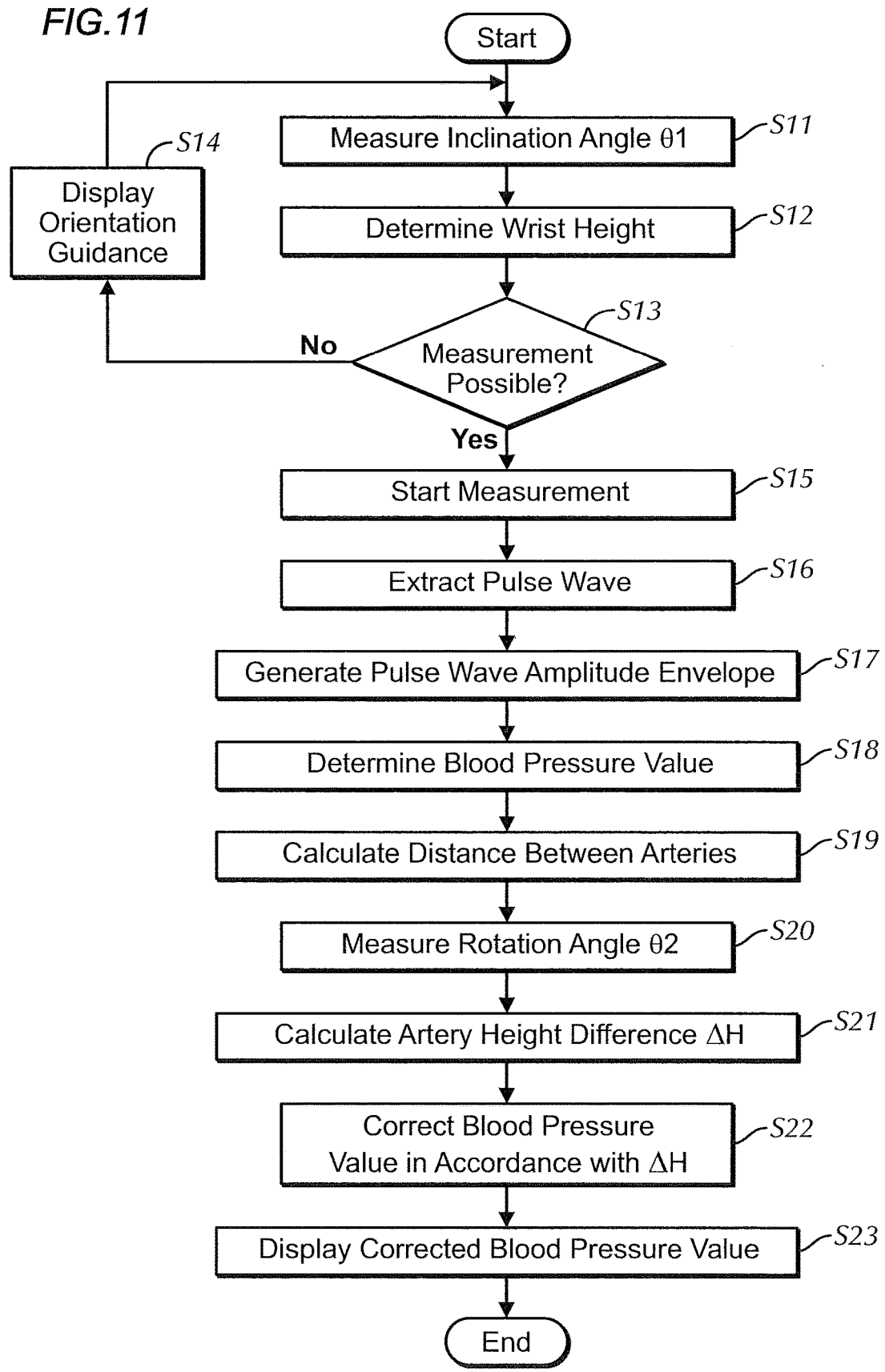
FIG. 11 is a flowchart for describing a modified example of an operation of the blood pressure measurement apparatus 1.

FIG. 11 is a flowchart for describing a modified example of an operation of the blood pressure measurement apparatus 1.

When the start of blood pressure measurement is instructed by operation of the operation unit 21, the CPU 20 measures the inclination angle θ1 of the forearm based on the information detected by the acceleration sensor 17 (step S11).

Next, the CPU 20 uses the inclination angle θ1 measured in step S11, and the information regarding the upper arm length L1, the forearm length L2, the angle θ3, the distance Ha from the shoulder S of the measurement subject 40 to the seat face of the chair CH, the seat face height Hb of the chair CH, and the height Hb of the table T to calculate ΔD using the calculation of equations (2) and (3) (step S12).

Based on ΔD calculated in step S12, the CPU 20 determines whether or not the orientation of the measurement subject is an orientation at which blood pressure measurement is possible (step S13).

If ΔD is less than or equal to the allowable value, the CPU 20 determines that it is an orientation at which blood pressure measurement is possible. If ΔD exceeds the allowable value, the CPU 20 determines that it is an orientation at which blood pressure measurement is not possible.

If the result of the determination in step S13 is NO, the CPU 20 calculates the inclination angle θ1 at which ΔD is less than or equal to the allowable value, and displays, on the display unit 19, information for guiding the measurement subject so that the inclination angle θ1 reaches the calculated angle (step S14). Then, the CPU 20 returns to the processing of step S11.

If the result of the determination of step S13 is YES, the CPU 20 starts the pressurization of the wrist by means of the cuff 30 and starts blood pressure measurement by means of the oscillometric method (step S15).

The CPU 20 extracts a pulse wave from the cuff pressure signal (step S16) and generates pulse wave amplitude envelope data (step S17). Then, the systolic blood pressure value and the diastolic blood pressure value are determined based on the pulse wave amplitude envelope data (step S18).

Next, the CPU 20 calculates the distance d between the radial artery and the ulnar artery, based on the image formed by the artery detection unit 18 (step S19). Also, the CPU 20 measures the rotation angle θ2 based on the information detected by the acceleration sensor 17 (step S20).

Then, the CPU 20 uses the inclination angle θ1 measured in step S11, the rotation angle θ2 measured in step S20, and the distance d calculated in step S19 to calculate ΔH using the calculation of equation (1) (step S21).

Next, the CPU 20 substitutes the systolic and diastolic blood pressures (each denoted as "P") determined in step S18 and ΔH calculated in step S21 into equations (4) and (5) so as to correct the systolic and diastolic blood pressures determined in step S18 (step S22).

Finally, the CPU 20 causes the value resulting from the correction in step S22 to be displayed on the display unit 19 (step S23) and ends the operation according to the blood pressure measurement instruction.

As described above, according to the blood pressure measurement apparatus 1 in which the CPU 20 shown in FIG. 8 is mounted, even if the blood pressure is measured in a state in which the height difference ΔH between the radial artery and the ulnar artery exceeds the allowable value, the blood pressure value determined by the blood pressure measurement unit 20a is corrected in accordance with the height difference ΔH, and therefore an accurate blood pressure value with no error can be measured.

Note that the embodiment disclosed above is to be understood as being in all ways exemplary and in no way limiting. Indeed, the scope of one or more embodiments of the claimed invention is defined not by the aforementioned description but by the scope of the appended claims.

The present specification discloses the following items.

The disclosed blood pressure measurement apparatus is a blood pressure measurement apparatus configured to be used while attached to a wrist of a measurement subject, and includes: an inclination angle measurement unit configured to measure an inclination angle, which is an angle formed by the forearm of the measurement subject with respect to a reference plane; a rotation angle measurement unit configured to measure a rotation angle about an axis, using the forearm as the axis, of the blood pressure measurement apparatus; a distance information acquisition unit configured to acquire distance information regarding the distance between the ulnar artery and the radial artery that pass through the wrist; a determination unit configured to determine a relative positional relationship between the radial artery and the ulnar artery using the inclination angle, the rotation angle, and the distance information; and a control unit configured to perform control according to the relative positional relationship.

With the disclosed blood pressure measurement apparatus, the control unit, in accordance with the relative positional relationship, outputs information for guiding the rotation angle to an angle at which the difference between the height from the reference plane of the radial artery and the height from the reference plane of the ulnar artery is less than or equal to a pre-determined value, and the control unit includes a blood pressure measurement unit configured to start measurement of blood pressure when it is determined by the determination unit that the difference between the height from the reference plane of the radial artery and the height from the reference plane of the ulnar artery is less than or equal to the predetermined value.

The disclosed blood pressure measurement apparatus includes a height detection unit configured to, using the inclination angle, detect the height of the wrist with respect to the heart of the measurement subject, wherein based on the height of the wrist and the relative positional relationship, the control unit outputs information for guiding the rotation angle and the inclination angle to angles at which the difference between the height from the reference plane of the radial artery and the height from the reference plane of the ulnar artery is less than or equal to a predetermined value and the height of the wrist with respect to the heart of the measurement subject is less than or equal to a predetermined value, and the control unit includes a blood pressure measurement unit configured to start measurement of blood pressure when it is determined by the determination unit that the difference between the height from the reference plane of the radial artery and the height from the reference plane of the ulnar artery is less than or equal to a predetermined value and the height detected by the height detection unit is less than or equal to a predetermined value.

The disclosed blood pressure measurement apparatus includes a blood pressure measurement unit configured to extract a pulse wave from the detected pressure in the cuff during a process of increasing or a process of reducing the pressure with which the cuff pressurizes the wrist and measure blood pressure based on an amplitude value of the pulse wave, wherein in accordance with the relative positional relationship, the control unit corrects the blood pressure value measured by the blood pressure measurement unit.

With the disclosed blood pressure measurement apparatus, as the relative positional relationship, the determination unit determines a difference ΔH between the height from the reference plane of the radial artery and the height from the reference plane of the ulnar artery and the magnitude relationship between the heights from the reference plane of the radial artery and the ulnar artery, and a value, which is obtained by multiplying the ΔH, a hydraulic head pressure per unit length, and a coefficient determined according to a ratio between a transmission rate of the pressure with which the cuff pressurizes the radial artery and a transmission rate of the pressure with which the cuff pressurizes the ulnar artery, is, in accordance with the magnitude relationship, added to or subtracted from the blood pressure value measured by the blood pressure measurement unit, and thereby the blood pressure value is corrected.

The disclosed blood pressure measurement apparatus includes a sensor configured to emit light to the wrist, receive light reflected from the wrist, and convert the light into an electrical signal, and a distance information generation unit configured to generate the distance information based on the output signal of the sensor.

The disclosed control method for the blood pressure measurement apparatus is a control method for a blood pressure measurement apparatus configured to be used while attached to a wrist of a measurement subject, the method including: an inclination angle measurement step of measuring an inclination angle, which is an angle formed by a forearm of the measurement subject with respect to a reference plane; a rotation angle measurement step of measuring a rotation angle about an axis, using the forearm as the axis, of the blood pressure measurement apparatus; a distance information acquisition step of acquiring distance information regarding the distance between the radial artery and the ulnar artery, which pass through the wrist; a determination step of determining a relative positional relationship between the radial artery and the ulnar artery using the inclination angle, the rotation angle, and the distance information; and a control step of performing control according to the relative positional relationship.

INDUSTRIAL APPLICABILITY

One or more embodiments of the claimed invention can be applied to a blood pressure meter for home use, for example, and is useful for managing the health of a user.

While the claimed invention has been described in detail with reference to a specific embodiment, it will be clear to one of ordinary skill in the art that many variations and modifications can be made without departing from the essential spirit and scope of the claimed invention. This application claims the benefit of Japanese Patent Application No. 2012-211139, filed Sep. 25, 2012, which is hereby incorporated by reference herein in its entirety.

REFERENCE SIGNS LIST

1 Blood pressure measurement apparatus
10 Main body portion
30 Cuff
11 Pressure sensor
17 Triaxial acceleration sensor
19 Display unit
20 CPU
20a Blood pressure measurement unit
20b Inter-artery distance information generation unit
20c Artery relative position determination unit
20d Wrist height detection unit
20e, 20e' Measurement orientation guidance unit
20f Blood pressure correction unit
20h Angle measurement unit
21 Operation unit
40 Measurement subject
50 Wrist
51 Radial artery
52 Ulnar artery
d Inter-artery distance
F Forearm
U Upper arm
θ1 Inclination angle
θ2 Rotation angle
ΔD Height difference between measurement site and heart H

The invention claimed is:

1. A blood pressure measurement apparatus configured to be used while attached to a wrist of a measurement subject, the blood pressure measurement apparatus comprising:
a cuff comprising an air bladder, wherein the cuff is configured to pressurize the wrist of the measurement subject to start blood pressure measurement; and
a main body portion attached to the cuff, the main body portion comprising a central processing unit that comprises:
an inclination angle measurement unit configured to measure an inclination angle, which is an angle formed by the forearm of the measurement subject with respect to a reference plane;
a rotation angle measurement unit configured to measure a rotation angle about an axis, using a forearm as the axis, of the blood pressure measurement apparatus;
a distance information generation unit configured to generate distance information regarding the distance between the ulnar artery and the radial artery that pass through the wrist;
a determination unit configured to determine a relative positional relationship between the radial artery and the ulnar artery using the inclination angle, the rotation angle, and the distance information;
a blood pressure measurement unit configured to extract a pulse wave from a detected pressure in the cuff during a process of increasing or a process of reducing the pressure with which the cuff pressurizes the wrist and measure blood pressure based on an amplitude value of the pulse wave; and
a control unit configured to correct the blood pressure measurement measured by the blood pressure measurement unit according to the relative positional relationship,
wherein the determination unit determines the relative positional relationship between the radial artery and the ulnar artery by determining a difference ΔH between the height from the reference plane of the radial artery and the height from the reference plane of the ulnar artery and the magnitude relationship between the heights from the reference plane of the radial artery and the ulnar artery,
wherein a value, which is obtained by multiplying the ΔH, a hydraulic head pressure per unit length, and a coefficient determined according to a ratio between a transmission rate of the pressure with which the cuff pressurizes the radial artery and a transmission rate of the pressure with which the cuff pressurizes the ulnar artery, is, in accordance with the magnitude relationship, added to or subtracted from the blood pressure value measured by the blood pressure measurement unit, and thereby the blood pressure value is corrected, and wherein the ratio between the transmission rate of the pressure with which the cuff pressurizes the radial artery and the transmission rate of the pressure with which the cuff pressurizes the ulnar artery is 1:1.

2. The blood pressure measurement apparatus according to claim 1, wherein the control unit, in accordance with the relative positional relationship, outputs information for guiding the rotation angle to an angle at which the difference between the height from the reference plane of the radial artery and the height from the reference plane of the ulnar artery is less than or equal to a predetermined value, and wherein the control unit includes a blood pressure measurement unit configured to start measurement of blood pressure when it is determined by the determination unit that the difference between the height from the reference plane of the radial artery and the height from the reference plane of the ulnar artery is less than or equal to the predetermined value.

3. The blood pressure measurement apparatus according to claim 1, further comprising:

a height detection unit configured to, using the inclination angle, detect the height of the wrist with respect to the heart of the measurement subject, wherein based on the height of the wrist and the relative positional relationship, the control unit outputs information for guiding the rotation angle and the inclination angle to angles at which the difference between the height from the reference plane of the radial artery and the height from the reference plane of the ulnar artery is less than or equal to a predetermined value and the height of the wrist with respect to the heart of the measurement subject is less than or equal to a predetermined value, and wherein the control unit includes a blood pressure measurement unit configured to start measurement of blood pressure when it is determined by the determination unit that the difference between the height from the reference plane of the radial artery and the height from the reference plane of the ulnar artery is less than or equal to a predetermined value and the height detected by the height detection unit is less than or equal to a predetermined value.

4. The blood pressure measurement apparatus according to claim 1, further comprising:

a sensor configured to emit light to the wrist, receive light reflected from the wrist, and convert the light into an electrical signal, wherein the distance information generation unit generates the distance information based on the electrical signal of the sensor.

5. The blood pressure measurement apparatus according to claim 2, further comprising:

a sensor configured to emit light to the wrist, receive light reflected from the wrist, and convert the light into an electrical signal, wherein the distance information generation unit generates the distance information based on the electrical signal of the sensor.

6. The blood pressure measurement apparatus according to claim 3, further comprising:

a sensor configured to emit light to the wrist, receive light reflected from the wrist, and convert the light into an electrical signal, wherein the distance information generation unit generates the distance information based on the electrical signal of the sensor.

7. A control method for a blood pressure measurement apparatus comprising a cuff configured to be used while attached to a wrist of a measurement subject, the method comprising:

an inclination angle measurement step of measuring an inclination angle, which is an angle formed by a forearm of the measurement subject with respect to a reference plane;

a step of pressurizing the wrist of the measurement subject to start blood pressure measurement using the cuff, which comprises an air bladder;

a rotation angle measurement step of measuring a rotation angle about an axis, using the forearm as the axis, of the blood pressure measurement apparatus;

a distance information generation step of generating distance information regarding the distance between the radial artery and the ulnar artery, which pass through the wrist;

a determination step of determining a relative positional relationship between the radial artery and the ulnar artery using the inclination angle, the rotation angle, and the distance information;

a blood pressure measurement step of extracting a pulse wave from a detected pressure in the cuff during a process of increasing or a process of reducing the pressure with which the cuff pressurizes the wrist and measuring blood pressure based on an amplitude of the pulse wave; and a control step of correcting the blood pressure measurement measured in the blood pressure measurement step according to the relative positional relationship, wherein the determination step determines the relative positional relationship between the radial artery and the ulnar artery by determining a difference $\Delta H$ between the height from the reference plane of the radial artery and the height from the reference plane of the ulnar artery and the magnitude relationship between the heights from the reference plane of the radial artery and the ulnar artery, wherein a value, which is obtained by multiplying the $\Delta H$, a hydraulic head pressure per unit length, and a coefficient determined according to a ratio between a transmission rate of the pressure with which the cuff pressurizes the radial artery and a transmission rate of the pressure with which the cuff pressurizes the ulnar artery, is, in accordance with the magnitude relationship, added to or subtracted from the blood pressure value measured by the blood pressure measurement unit, and thereby the blood pressure value is corrected, and wherein the ratio between the transmission rate of the pressure with which the cuff pressurizes the radial artery and the transmission rate of the pressure with which the cuff pressurizes the ulnar artery is 1:1.

* * * * *